(12) United States Patent
Dave et al.

(10) Patent No.: US 6,665,456 B2
(45) Date of Patent: Dec. 16, 2003

(54) METHOD AND APPARATUS FOR DIFFERENTIAL PHASE OPTICAL COHERENCE TOMOGRAPHY

(75) Inventors: Digant P. Dave, Austin, TX (US); Thomas E. Milner, Austin, TX (US); Sergey Telenkov, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/044,421

(22) Filed: Jan. 11, 2002

(65) Prior Publication Data

US 2003/0020920 A1 Jan. 30, 2003

Related U.S. Application Data (60) Provisional application No. 60/261,658, filed on Jan. 12, 2001.

(51) Int. Cl.[7] .............................. G02B 6/27; G01B 9/02; G01J 4/00
(52) U.S. Cl. .......................... 385/11; 385/15; 356/477; 356/491; 356/369
(58) Field of Search .............................. 385/1–3, 11, 12, 385/15; 356/450, 477–479, 491, 364, 369

(56) References Cited

U.S. PATENT DOCUMENTS

| | | | | | |
|---|---|---|---|---|---|
| 3,684,350 | A | * | 8/1972 | Wentz | 359/256 |
| 5,434,669 | A | * | 7/1995 | Tabata et al. | 356/345 |
| 5,526,115 | A | * | 6/1996 | Nishiura | 356/350 |
| 5,559,784 | A | * | 9/1996 | Ota | 369/124 |

* cited by examiner

*Primary Examiner*—John D. Lee
(74) *Attorney, Agent, or Firm*—Gardere Wynne Sewell LLP (57) ABSTRACT

One form of the present invention is a dual channel optical reflectometer composed of a birefringent path coupler and an optical source path that is optically connected to the path coupler. After entering the path coupler, light is split into birefringent reference and sample paths. The reference path is optically aligned with a first collimating lens, and the collimating lens is directed into a scanning delay line. There is also a birefringent optical sample path that is also optically connected to the path coupler. The sample path is optically aligned with a polarization channel separator/combiner and a lens, to focus and direct optical beams into the turbid sample. Light backscattered from the turbid sample is collected by the second lens and orthogonal polarization channels are reunited by the polarization channel combiner. An analog-to-digital converter is connected to the amplifier, and a computer is connected to the analog-to-digital converter to analyze the output.

30 Claims, 4 Drawing Sheets

METHOD AND APPARATUS FOR DIFFERENTIAL PHASE OPTICAL COHERENCE TOMOGRAPHY

This application claims priority from Provisional Patent Application Ser. No. 60/261,658, filed Jan. 12, 2001.

The present invention relates generally to the field of optics and in particular to an interferometric system that may detect dynamic phenomenon in turbid media as well as particle movement velocity and direction using differential phase measurements.

BACKGROUND OF THE INVENTION

Optical low-coherence reflectometry has been used extensively in ranging of optical components and more recently in optical coherence tomography (OCT) for imaging turbid media such as tissues. Previous application of OCT to image turbid media have relied on envelope detection of the interference fringe intensity to construct pixelated tomographic images. Phase sensitive detection of the interference fringe intensity can dramatically improve the resolution of optical low-coherence tomography, especially in objects in which reflectivity contrast is poor, or sub-wavelength changes in optical path length are being measured.

In a single-channel-fiber Michelson interferometer, accurate phase sensitive detection of the interference fringe intensity is difficult because of the presence of phase noise. Environmental perturbations, including temperature fluctuations, air currents, vibration, mechanical movements and phase modulation contribute to the phase noise. Elimination of phase noise in an interferometer is usually difficult and expensive. Accurate phase detection is especially difficult in optical fiber interferometers used to image tissue structures where environmental perturbations result not only in phase fluctuations for optical signals of each light polarization incident on the sample but also random variation between phases in orthogonal polarization channels. Moreover, random phase variations in optical fiber interferometers between orthogonal polarization channels results in a variable light polarization state incident on the sample.

Conventional methods for accurate phase sensitive detection of the interference fringe intensity require careful monitoring of any optical path length variations in the interferometer. Unfortunately, application of these methods is limited principally to bulk interferometric systems in air and are not easily adapted to fiber based instruments. One can dramatically reduce phase noise by performing differential phase measurement, since the common-mode phase noise is canceled. A fiber optic interferometer is described that allows measurement of the differential phase between two de-correlated optical signals incident on and returned from a turbid sample.

Differential phase measurement between optical signals in two decorrelated interferometric channels can be applied to measure accurately and image many phenomenon in turbid media. For example, the Doppler effect arises when the optical phase of light backscattered from an object is modified due to particle movement along the light propagation direction. Conventional Doppler optical coherence tomography is a useful tool for noninvasive fluid-flow measurements in highly scattering media. Two advantages of Doppler optical coherence tomography are high spatial resolution (3–15 microns) and extraordinary volumetric flow sensitivity (40–108 pL/s).

With Doppler optical coherence tomography one can monitor flow velocities at a discrete location in a highly scattering medium. In conventional Doppler OCT, flow velocity is estimated from the Doppler-shifted interference signal formed between light backscattered from the flowing fluid in the sample path and light retroreflected from the reference path in a Michelson interferometer. The measured Doppler shift is dependent on the difference between the incident and the scattered lightwave vectors, which is referred to as the Doppler angle.

Inasmuch as the Doppler-shifted interference signal is a function of the Doppler angle, inaccurate values of the angle will limit the accuracy of flow-velocity estimation. In many applications accurate estimation of the Doppler angle is difficult if not impossible, particularly when the flow is buried in a highly scattering medium (e.g., for in vivo blood flow monitoring). A dual probe-beam setup is used in ultrasonic color flow mapping (two transducers) and laser Doppler anemometry (two lasers) for accurate estimation of flow velocity. The claimed subject matter of the present invention includes a novel dual-channel optical low-coherence reflectometer (OLCR) in which two probe beams are oriented at a precisely known relative orientation that allows for measurement of differential phase of the optical signals backscattered from a turbid sample.

Measurement of the differential phase may be used to detect dynamically subwavelenth particle movements (blood flow), molecular re-orientations (neural action potential propagation), acoustic wave mechanical displacements, thermal induced motions, or electro-chemical reactions. Although we recognize the interferometric system described may be utilized to detect in turbid media any of the indicated dynamic phenomenon, we focus our description on differential phase measurements to determine particle movement velocity and direction.

SUMMARY OF THE INVENTION

Differential phase measurement in turbid or highly scattering media has long been recognized as a difficult problem. Generally, and in one form of the present invention, the use of two probe beams oriented at a preset orientation allows the measurement of the Doppler frequency shift in a highly light scattering sample.

More specifically, one form of the present invention is a dual channel optical reflectometer composed of a birefringent path coupler and an optical source path that is optically connected to the path coupler. Broad bandwidth light entering the path coupler is depolarized by propagating light through a Lyot depolarizer or equivalent acting optical component. Light entering the path coupler consists of two de-correlated optical signals in orthogonal polarization channels. The path coupler must separate light into birefringent sample and reference paths while maintaining energy separation and decorrelation of optical signals in the fast and slow fiber polarization channels. After entering the path coupler, light is split into birefringent reference and sample paths.

The reference path is optically aligned with a first collimating lens, and the collimating lens is directed into a scanning delay line. There is also a birefringent optical sample path that is also optically connected to the path coupler. The sample path is optically aligned with a second collimating lens, a polarization channel separator/combiner and a lens, to focus and direct optical beams into the turbid sample. In the current embodiment, a Wollaston prism is utilzed as a static polarization channel separator/combiner. In other embodiments, a Rochon prism or similar acting optical device may be used as a dynamic or static polarization channel separator/combiner. In the current embodiment, the Wollaston prism is oriented so that optical signals in the two orthogonal and de-correlated polarization channels are separated to propagate in different directions.

The relative orientation of the light propagation vectors of light in the two orthogonal and decorrelated polarization channels is specified by the cut angle and material birefringence of the Wollaston prism. In the current embodiment, the second lens is positioned so that the cut-interface of the Wollaston prism and the point in the sample under investigation are at conjugate image planes. In this configuration, light in the two decorrelated polarization channels are brought to a common focus in the turbid sample at the point under investigation. Light backscattered from the turbid sample is collected by the second lens and orthogonal polarization channels are reunited by the polarization channel combiner. In the current embodiment, the Wollaston prism serves as both a static polarization channel separator and combiner.

A birefringent optical detection path is optically connected to the path coupler. A second polarization separator divides light in the two decorrelated polarization channels into different propagation directions and optically coupled to first and second photoreceivers that produce first and second output signals, respectively. The first and second output signals pass through a bandpass filter and amplifier. An analog-to-digital converter is connected to the amplifier, and a computer is connected to the analog-to-digital converter.

Another form of the invention is a dual channel reflectometer composed of a path coupler and a source path that is further composed of a first birefringent optical fiber having first and second ends. The first end of the first optical fiber is optically coupled to a light source and splits the light source into a first and second decorrelated polarization channels with independent phase components. The second end of the first optical fiber is connected to a depolarizer.

A second birefringent optical fiber having a first and a second end, has its first end connected to the depolarizer, and the second end of the second optical fiber is optically connected to the path coupler. The path coupler must separate light into birefringent sample and reference paths while maintaining energy separation and decorrelation of optical signals in the fast and slow fiber polarization channels.

There is also a reference path that is composed of a third birefringent optical fiber having first and second ends. The first end of the third optical fiber is optically connected to the path coupler. The second end of the third optical fiber is optically aligned with a first collimating lens that collimates light emitting from the second end of the third collimating fiber into a scanning delay line that includes a galvanometer that allows a variable phase modulation frequency.

There is also a sample path composed of a fourth birefringent optical fiber having a first and second end. The first end of the fourth optical fiber is optically connected to the path coupler. The second end of the fourth optical fiber is optically aligned with a second collimating lens that collimates light emitting from the second end of the fourth fiber and propagates through a first polarization separator (e.g., Wollaston prism) and a focusing lens, where the focusing lens is aligned so that the two decorrelated polarization channels with independent phase components are focused at a single point in a sample.

There is also a detection path composed of a fifth birefringent optical fiber having first and second ends. The first end of the fifth optical fiber is optically connected to the path coupler. The second end of the fifth optical fiber is aligned with a third collimating lens that collimates light emitting from the second end of the fifth optical fiber onto a second polarization separator (e.g., Wollaston prism) that separates the light from the fifth optical fiber into a first and a second beam, each beam corresponding to one phase component.

A first photodetector detects the first beam and produces a first output signal, and the second photodetector detects the second beam and produces a second output signal. The first and second output signals pass through a bandpass filter and amplifier. An analog-to-digital converter is attached to the filter-amplifier, and a computer is attached to the analog-to-digital converter.

In another form of the present invention, a birefringent optical fiber path is optically aligned with a collimating lens, a polarization channel separator/combiner (e.g., Wollaston prism) and a focusing lens such that the focusing lens focuses light beams corresponding to the two decorrelated polarization channels to a single point in the turbid sample.

In another form of the present invention, a birefringent optical fiber sample path is optically aligned with a collimating lens, a polarization channel separator/combiner (e.g., Wollaston prism) that produces two beams, and a focusing lens. The two beams are collinear and contain decorrelated optical signals that are longitudinally displaced relative to each other. "Longitudinal displacement" in this application means that the points of interest in the two beams are along the same line from, but at different distances from, a point of reference. The longitudinal displacement may be static or time-dependent and may be (but not necessarily) implemented using a static or time-dependent polarization separator/combiner in the sample path.

In another form of the present invention a birefringent optical fiber sample path is optically aligned with a collimating lens, and a polarization channel separator/combiner. Optical signals in the two separated beams are decorrelated. The polarization channel separator/combiner produces two beams, wherein the two beams are horizontally separated relative to one another, and the horizontal separation is time dependant. "Time dependant" in this application means that the degree of separation between the two beams changes as function of time. "Horizontal" is defined in this application as being the plane containing the two beam propagation directions. The horizontal displacement may be static or time-dependent and may be (but not necessarily) implemented using a static or time-dependent polarization separator/combiner in the sample path.

In yet another form the present invention provides a birefringent optical reference path that includes a phase modulator. The phase modulator may be, but is not limited to, a lithium niobate Y-waveguide electro-optic phase modulator.

BRIEF DESCRIPTION OF THE DRAWINGS

The above and further advantages of the invention may be better understood by referring to the following description in conjunction with the accompanying drawings in which corresponding numerals in different figures refer to corresponding parts in which.

DETAILED DESCRIPTION

While the making and using of various embodiments of the present invention are discussed herein in terms of a dual channel optical reflectometer apparatus and method, it should be appreciated that the present invention provides many applicable inventive concepts that may be embodied in a wide variety of specific contexts. The specific embodiments discussed herein are merely illustrative of specific ways to make and use the invention and are not intended to limit the scope of the invention.

One form of the present invention provides a method and apparatus for accurately measuring the Doppler frequency shift of two convergent beams reflected from moving constituents imbedded in a medium. This allows for a precise determination of the flow velocity of the moving constituents. Moreover, this measurement can be applied to produce a pixelated tomographic image of the flow velocity of moving constituents in the medium. The present invention is applicable to a wide variety of sample types. The present invention is particularly applicable to measuring Doppler frequency shifts of moving constituents that are present in highly light-scattering media, such as the measurement of in vivo blood flow in tissue.

Figure 1:
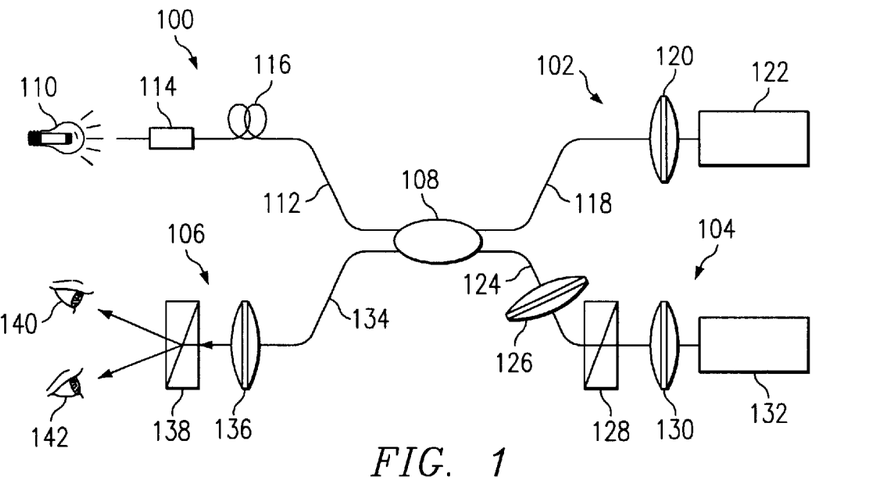
FIG. 1 is a schematic diagram of a dual channel optical reflectometer in accordance with the present invention.

FIG. 1 shows a dual channel optical reflectometer. The dual channel optical reflectometer is composed of four separate paths 100, 102, 104, and 106 interconnected through a path coupler 108. The source path 100 is comprised of a light source 110 that is optically coupled to a birefringent optical fiber 112. A depolarizer 114 is placed in-line in the optical fiber 112. The optical fiber 112 is of sufficient length 116 to insure complete decorrelation of the polarization channels with independent phase components that are separated by virtue of the birefringent nature of the optical fiber 112. The source path is optically connected to the path coupler 108.

The reference path 102 is comprised of another birefringent optical fiber 118 that is optically connected to the path coupler 108 on one end, and has the other end optically aligned with a collimating lens 120 that collimates the light emitted from the second end of optical fiber 118 into a scanning delay line 122. The sample path 104 is comprised of another birefringent optical fiber 124 that is optically connected to the path coupler 108 on one end, and the other end is optically aligned with a collimating lens, a Wollaston prism 128, and a focusing lens 130. The alignment is such that the focusing lens focuses the two decorrelated phase-component beams of light to a single point on a sample 132 where the precise angle between the focused beams is known.

The detector path 106 is comprised of yet another birefringent optical fiber that is optically connected to the path coupler 108 at one end, and the other end is optically aligned with a collimating lens 136 and a Wollaston prism 138. The Wollaston prism separates the two decorrelated phase-component beams and each is detected by a separate photodetector 140 and 142.

Figure 2:
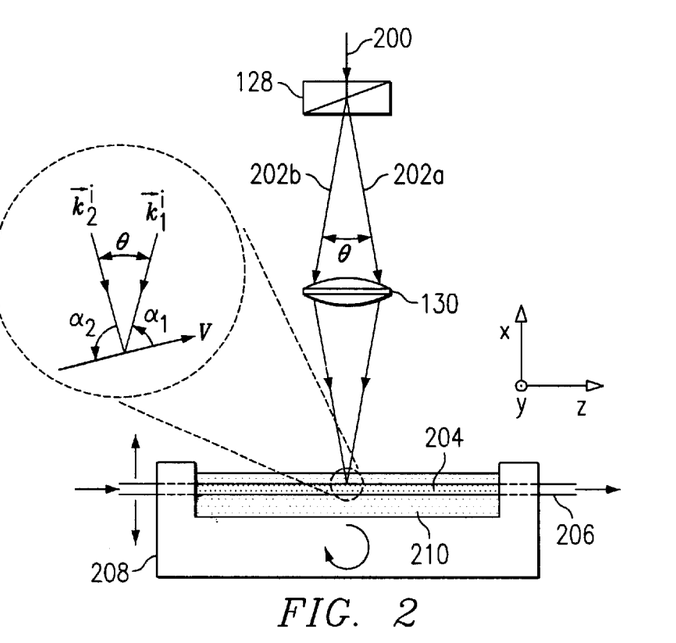
FIG. 2 is a view of a portion of a sample path of a dual channel reflectometer in accordance with the present invention.

FIG. 2 shows a portion of the sample path in more detail. The incoming birefringent light source 200 is split into separate beams with decorrelated phase components 202a and 202b by the Wollaston prism 128. The focusing lens 130 is aligned so that it focuses the phase-component beams at a single point in a sample. In FIG. 2 the sample 204 is flowing through a capillary 206. The capillary is submerged in a trough 208. Both the sample flowing through the capillary and the media used to fill the trough 210 were highly light scattering Intralipid solution.

The inset in FIG. 2 shows the probe beams as $k^i_1$ and $k^i_2$ at an angle $\theta$ relative to one another. The Doppler angles are represented by $\alpha_1$ and $\alpha_2$ and the flow velocity of the sample is V.

The Doppler frequency shifts in each channel are given by $$\Delta f_{1,2} = \frac{1}{2\pi}(k^s_{1,2} - k^i_{1,2}) \cdot V,$$

where $k_{1,2}{}^i$ and $k_{1,2}{}^s$ are the wave vectors of the incident and the scattered light in air, respectively, for channel n(=1,2) and V is the flow-velocity vector. We assume that the incident and the scattered light directions are colliner ($k_{1,2}{}^i = -k_{1,2}{}^s$) and that the probe beams and the flow-velocity vector are in the same plane [$k_2 \cdot (k_1 \times V) = 0$]. From Eq. (1), the Doppler angles for the two probe beams are $$\alpha_1 = \arctan\left(\tan\theta - \frac{\Delta f_2}{\Delta f_1 \sin\theta}\right),$$

$$\alpha_2 = \pi - \theta - \alpha_1$$

where $\theta$ is the divergence angle of the Wollason prism and the fluid-flow velocity is $$V = \frac{\Delta f_{1,2} \lambda}{2\cos\alpha_{1,2}}$$

A 1% Intralipid solution flowing in a cylindrical glass capillary was chosen to demonstrate the technique. The inner and outer diameters of the capillary were 0.53 and 1.55 mm, respectively. The Intralipid flow was controlled with a syringe pump with a Teflon tube that was attached to the capillary. A trough (50 mm×40 mm×6.25 mm) containing the capillary tube was mounted upon a goniometer fastened to a linear translation stage. The interference fringes in the two decorrelated polarization channels were recorded along a line passing through the center of the capillary tube by translating the trough-tube assembly in depth (axis).

The Doppler angles ($\alpha_1$ and $\alpha_2$) between the probe beams and the capillary tube were varied by tilting (rotation about the y axis) the goniometer. The base phase modulation frequency and scan rate were set to 28.2 kHz and 100 Hz, respectively. For each depth scan we collected Doppler-shifted interference signal data over a depth of approximately 40 μm. To ensure that the two probe beams interrogated the same point in the flowing fluid, the sample was translated in depth.

Figure 3A:
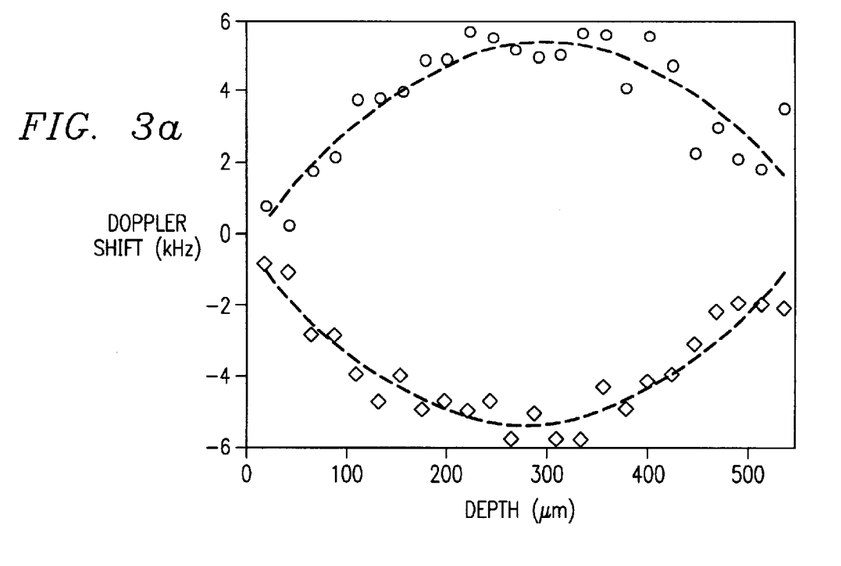
FIGS. 3a–3d show the Doppler shift as a function of depth in channel 1 (circles) and channel 2 (diamonds) owing to a flowing intralipid solution in a glass capillary submerged in a turbid medium.
Figure 3B:
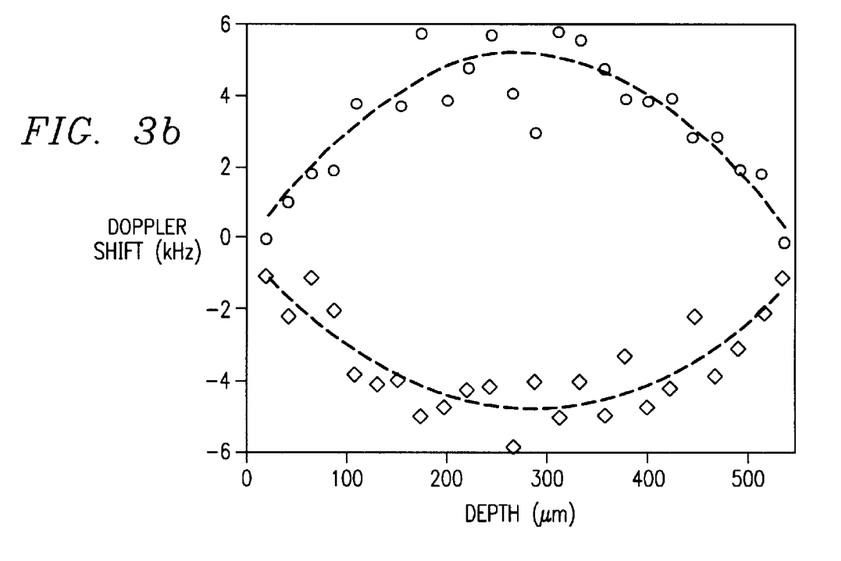
Figure 3C:
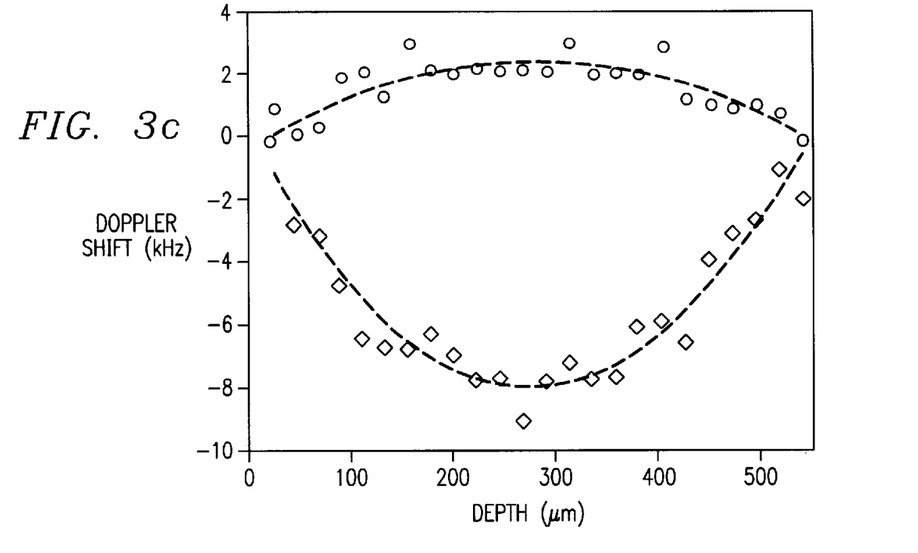
Figure 3D:
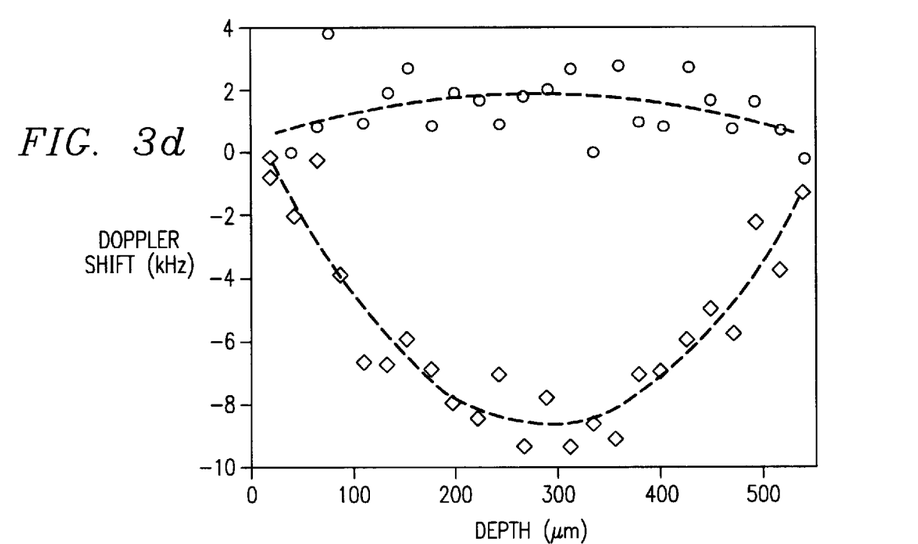

The Doppler shift in the two decorrelated polarization channels, defined as channels 1 and 2, was measured as a function of depth with the capillary tube in air [FIGS. 3(a) and 3(c)] and with the tube immersed in a 1% Intralipid solutions [FIGS. 3(b) and 3(d)]. For FIGS. 3(b) and 3(d) the top of the capillary tube was approximately 1 mm below the air-Intralipid inter-face. The immersed capillary tube was not visible to the naked eye owing to the high scattering in the Intralipid solution. Intralipid solution is commercially available, and is used to mimic scattering properties of media such as biological tissues and blood. The Wollaston prism was oriented such that the wave vectors of the two probe beams and the flow-velocity vector were in the same plane. For a fixed value of θ, this configuration ensures that the Doppler shift in each channel is maximum.

Each data point in FIG. 3 represents the difference between the centroid of the Doppler-shifted spectrum and the base phase-modulation frequency at one depth in the capillary tube. The bandwidth used for centroid calculation was fixed for each depth point. To improve the signal-to-noise ratio we averaged the Fourier transforms of 40 measurements at each depth and computed the centroid. As expected, the Doppler shift in the two channels is symmetrical when $\alpha_1 = \alpha_2$ [FIGS. 3(a) and 3(b)] and asymmetrical when $\alpha_1 \neq \alpha_2$ [FIGS. 3(c) and 3(d)]. We observed that simply calculating the centroid of the Doppler spectra within a fixed bandwidth underestimated Doppler frequency shifts in the two channels.

To obtain better estimates of the Doppler shift we used a modified centroid algorithm. First the peak in the Doppler spectra was identified; then the centroid of the power at frequencies distributed symmetrically (±4 kHz) about the peak was calculated. Values of $\alpha_1$ and $\alpha_2$ determined from the goniometer and experimental data are in excellent agreement. The calculated Doppler angles are an average of the values over the entire cross section of the capillary. The slight increase in error of the estimated Doppler angle when the capillary is buried in Intralipid solution can be attributed to the increase in Doppler noise for FIGS. 3(b) and 3(d) the capillary tube was immersed in 1% Intralipid solution. The dotted-dashed curves in each figure are the parabolic fits to the measured data owing to multiple scattering and increased signal attenuation. Note that the estimated Doppler angle is minimally affected by the choice of the algorithm used for calculating the centroid because the Doppler angle is proportional to the ratio of the Doppler shifts in the two channels. The calculated average velocity of the flowing Intralipid solution is comparable with the flow velocity of 11.5 mm/s computed from the preset flow rate.

Figure 4:
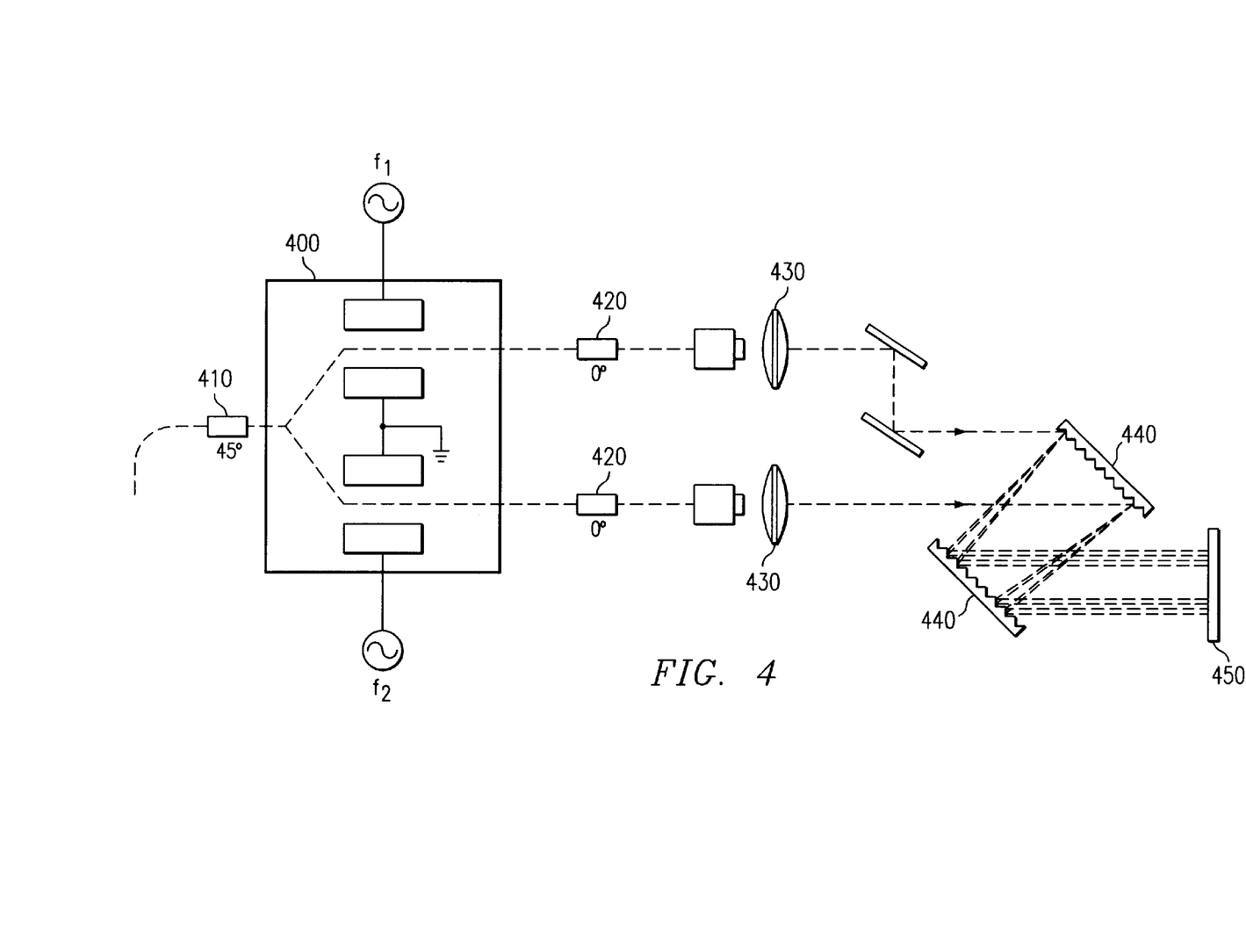
FIG. 4 is a view of a birefringent optical reference path containing an in-line phase modulator, in accordance with the present invention.

A further embodiment of the present invention incorporates an electro-optic phase modulator 400 in the reference path as depicted in FIG. 4. Inclusion of the electro-optic phase modulator provides a very stable phase modulation and measurement of fast transient differential phase changes in samples with improved accuracy. Since the electro-optic phase modulator accepts light in only one polarization channel, use in a dual polarization channel interferometer incorporating birefringent optical fibers requires careful optical design and splicing of fiber segments to preserve the dual channel operation of the interferometer.

The interferometer is an all fiber dual channel Michelson interferometer constructed with birefringent fiber. Single mode partially polarized light emitted from an optical semiconductor amplifier ($\lambda_0 = 1.3$ μm and $\Delta\lambda_{FWHM} = 60$ nm) is first polarized and input into a fiber Lyot depolarizer. Depolarization ensures that the polarization channels are completely decorrelated and that equal amplitudes are coupled into each fiber polarization mode. At the input to the 2×2 coupler, two independent and decorrelated linearly polarized modes propagate along birefringent axes of the fiber forming two signal channels denoted as fast (f) and slow (s). Light splits nearly equally into the reference and sample paths at the 2×2 coupler. Back reflected light from the object under test in the sample path and reference arm mix at the 2×2 coupler to form an interference signal.

In the reference path, output of the coupler fiber is spliced at 45° 410 to the input birefringent fiber of a Lithium Niobate (LiNbO$_3$) Y-waveguide electro-optic phase modulator so that both modes of the coupler are equally coupled into the slow axis of the phase modulator input birefringent fiber. Only light propagating along the slow axis of the birefringent fiber pigtailed to the phase modulator is launched into the TE mode of the integrated optic waveguide. Light splits equally into the two arms of the LiNbO$_3$ Y-waveguide phase modulator 400. Optical signals in each arm can be independently phase modulated from 0–500 MHz.

To avoid phase jumps in the interference signals at the interferometer output, phase modulators are driven with a ramp waveform with voltage amplitude that gives an integral multiple of π phase delay. Output of each Y waveguide arm is also pigtailed to a birefringent fiber. Both output fibers are spliced at 0° 420 to birefringent fibers terminated with FC/APC connectors and attached to collimators 430. Collimated light from the output fibers enter a dispersion compensating delay line that consists of a pair of diffraction gratings 440 and an end mirror 450. The function of the grating pair is to compensate chromatic and waveguide dispersion introduced by the Y-waveguide LiNbO$_3$ phase modulator. Dispersion if left uncompensated increases the width of the coherence function tenfold thereby drastically reducing the longitudinal resolution of the system.

Interference signals formed in the f and S channels will overlap only if optical path-length difference between sample and reference paths for each channel is equal. Since the coupler fiber lengths in reference and sample paths are equal and f and S channels travel the same optical path-length in the reference path after the 45° splice, the fiber geometry attached to the coupler fiber in the sample path should ensure that f and S optical signals propagate equivalent optical path lengths.

With the described configuration in the reference path, when any single segment of biregringent fiber is attached to the coupler fiber in the sample path, unequal optical path lengths between the f and s channels will result. By splicing together two equal segments of birefringent fiber at 90°, the path-length traversed by optical signals in f and s channels in the two-segment length become equal. In the sample path, one end of segment A is spliced at 0° to the coupler fiber and the other end is spliced to segment B at 90°. Fiber lengths of segments A and B are equivalent. The 90° splice interchanges the two channels (i.e., the s channel completely couples into the f and vice versa). Segment B is terminated with a FC/APC connector which is attached to a collimator.

Spatial and temporal separation of f and s channels in a sample can be achieved with a polarization channel separator/combiner (e.g., Wollaston prism). When the phase modulators in the Y-waveguide are driven with different frequencies, the concepts of frequency multiplexing and coherent multiplexing can be used to provide a four-channel conventional OLCR or a dual-channel differential phase OLCR.

In the detector path, f and s channels are separated using a polarization channel separator and directed onto respective photoreceivers. The photoreceivers are connected to a two-channel 12 bit analog-to-digital converter and stored in computer memory for processing. Frequency multiplexed signals are separated by digital filtering and then phase of each frequency channel is calculated by computing the arctangent of the filtered signal divided by its Hilbert transform.

What is claimed is:
1. A dual channel optical reflectometer comprising:
   a broad bandwidth optical light source;

an optical source path incorporating a depolarizing element that decorrelates optical signals in orthogonal fiber polarization channels and optically connects both channels to a path coupler;

a path coupler that separates light into birefringent sample and reference paths while maintaining energy separation and decorrelation of optical signals in the fast and slow fiber polarization channels;

a birefringent optical reference path optically connected to the path coupler and optically coupled to a scanning delay line;

a birefringent optical sample path optically connected to the path coupler, wherein the birefringent sample path comprises a polarization channel separator/combiner, wherein the polarization separator-combiner divides/reunites optical signals in fast and slow polarization channels into two distinct optical beams that intersect at a single point in the sample under test, wherein the polarization channel separator is optically connected to a beam combiner that reunites optical signals in fast and slow polarization channels;

the birefringent reference and sample paths are configured so that optical path length differences between fiber reference and sample paths in the fast and slow channels are less than one-half wavelength of incident light;

a birefringent optical detection path optically connected to the path coupler and a polarization channel separator that is optically coupled to a first and second photoreceivers that produce first and second output signals, respectively, wherein the first and second output signals pass through a bandpass filter and amplifier;

an analog-to-digital converter connected to the bandpass filter-amplifier; and a computer connected to the analog-to-digital converter.

2. The dual channel reflectometer as recited in claim 1, where the light source is an optical semiconductor amplifier.

3. The dual channel reflectometer as recited in claim 1, where the light source is an optical semiconductor amplifier centered at 1.3 microns and with a FWHM of about 60 nm.

4. The dual channel reflectometer as recited in claim 1, wherein the path coupler is a 2×2 phase-maintaining coupler.

5. The dual channel optical reflectometer as recited in claim 1, wherein the analog-digital converter is a 12-bit converter.

6. The dual channel optical reflectometer as recited in claim 1, wherein the source path further comprises a depolarizer.

7. The dual channel optical reflectometer as recited in claim 6, wherein the depolarizer is a Lyot depolarizer.

8. A dual channel optical reflectometer comprising:

a path coupler that separates light into birefringent sample and reference paths while maintaining energy separation and decorrelation of optical signals in orthogonal fiber polarization channels;

a source path comprising a first birefringent optical fiber having a first end and a second end;

the first end of the first optical fiber optically coupled to a light source and splitting the light source into a first and second polarization channels with independent phase components;

the second end of the first optical fiber connected to a depolarizer;

a second birefringent optical fiber having a first end and a second end, and the first end of the second optical fiber connected to the depolarizer; and the second end of the second optical fiber optically connected to the path coupler;

a reference path comprising a third birefringent optical fiber having a first end and a second end;

the first end of the third optical fiber optically connected to the path coupler;

the second end of the third optical fiber optically aligned with a first collimating lens that collimates, wherein the first collimating lens collimates light emitting from the second end of the third optical fiber into a rapid scanning delay line that includes a galvanometer that allows a variable phase modulation frequency;

a sample path comprising a fourth birefringent optical fiber having a first and a second end;

the first end of the fourth optical fiber optically connected to the path coupler;

the second end of the fourth optical fiber optically aligned with a second collimating lens, wherein the second collimating lens collimates light emitting from the second end of the fourth optical fiber through a first Wollaston prism and a focusing lens, wherein the focusing lens is aligned so that the light with two decorrelated polarization channels with independent phase components are focused at a single point on a sample;

a detection path comprising a fifth birefringent optical fiber having a first end and a second end;

the first end of the fifth optical fiber optically connected to the path coupler;

the second end of the fifth optical fiber optically aligned with a third collimating lens, wherein the third collimating lens collimates the light emitting from the fifth optical fiber onto a second Wollaston prism, wherein the second Wollaston prism splits the light from the fifth optical fiber into a first beam and a second beam, each beam corresponding to one phase component;

a first photodetector detects the first beam and produces a first output signal;

a second photodetector detects the second beam and produces a second output signal;

the first and second output signals pass through a bandpass filter and amplifier to produce a first and a second filtered signal;

an analog-to-digital converter is connected to the bandpass filter-amplifier; and a processor is connected to the analog-to-digital converter.

9. The dual channel optical low-coherence reflectometer as recited in claim 8, wherein the depolarizer is a decorrelator comprising a birefringent crystal or a segment of a birefringent fiber, selectively, with fast and slow axes aligned to the orthogonal polarization channels of the reflectometer.

10. The dual channel reflectometer as recited in claim 8, wherein the galvanometer has a scan rate of 180 Hz and the phase modulation frequency is 30 kHz.

11. The dual channel reflectometer as recited in claim 8, wherein the light source is a broadband light source.

12. The dual channel reflectometer as recited in claim 8, where the light source is an optical semiconductor amplifier.

13. The dual channel reflectometer as recited in claim 8, where the light source is an optical semiconductor amplifier centered at 1.3 microns and with a FWHM of about 60 nm.

14. The dual channel reflectometer as recited in claim 8, wherein the path coupler is a 2×2 polarization-maintaining coupler.

15. The dual channel reflectometer as recited in claim 8, wherein galvanometer has a scan rate of 180 Hz and the phase modulation frequency is 30 kHz.

16. The dual channel optical reflectometer as recited in claim 8, wherein the analog-digital converter is a 12-bit converter.

17. The dual channel optical reflectometer as recited in claim 8, wherein the analysis of the output comprises calculation of the Doppler frequency shift.

18. The dual channel optical reflectometer as recited in claim 8, wherein the sample comprises a highly light-scattering media.

19. The dual channel optical reflectometer as recited in claim 8, wherein the sample is in vivo blood flow.

20. The dual channel optical reflectometer as recited in claim 8, wherein the second birefringent optical fiber is at least two meters in length.

21. A birefringent optical fiber sample path optically aligned with an optical component disposed to inject decorrelated light into the optical fiber sample path comprising two decorrelated light signals in orthogonal polarization channels, the sample path being further optically aligned with a collimating lens, a Wollaston prism and a focusing lens, wherein the focusing lens is disposed to focus optical beams of decorrelated light corresponding to the decorrelated polarization channels to a single point in a sample.

22. The birefringent optical fiber sample path as recited in claim 21, wherein the sample comprises a highly light-scattering media.

23. The birefringent optical fiber sample path as recited in claim 21, wherein the sample is in vivo blood flow.

24. A method for measuring a Doppler-angle between light propagation and flow velocity vectors and comprising the steps of:

creating an optical source path;

creating an optical reference path that is optically coupled to a first collimating lens, wherein the collimating lens is directed into a rapid scanning delay line;

creating an optical sample path that is optically coupled to a second collimating lens, a first Wollaston prism, and a focusing lens, wherein the focusing lens focuses to a single point on a sample;

creating a birefringent optical detection path optically coupled to a third collimating lens and a second Wollaston prism, wherein the second Wollaston prism is optically coupled to first and second photoreceivers that produce first and second output signals, respectively, wherein the first and second output signals pass through a bandpass filter and amplifier to produce first and second filtered signals;

connecting the source path, the reference path, the sample path and the detection path to a path coupler;

converting the first and second filtered signals with an analog-digital converter; and connecting a computer to the analog-digital converter for data analysis.

25. A birefringent optical fiber sample path optically aligned with an optical component disposed to inject decorrelated light into the optical fiber sample path comprising two decorrelated light signals in orthogonal polarization channels, the sample path being further optically aligned with a collimating lens, a Wollaston prism that produces two beams of decorrelated light, and a focusing lens, wherein the two beams of decorrelated light are collinear and longitudinally displaced relative to each other.

26. The birefringent optical fiber sample path recited in claim 25, wherein the longitudinal displacement of the two beams relative to one another is time dependant.

27. A birefringent optical fiber sample path optically aligned with an optical component disposed to inject decorrelated light into the optical fiber sample path comprising two decorrelated light signals in orthogonal polarization channels, the sample path being further optically aligned with a collimating lens, a Wollaston prism that produces two beams of decorrelated light, and a focusing lens, wherein the two beams of decorrelated light are horizontally separated relative to one another, and the horizontal separation is time dependent.

28. A birefringent optical fiber reference path optically aligned with an optical component disposed to inject decorrelated light into the optical fiber reference path comprising two decorrelated light signals in orthogonal polarization channels, the optical fiber reference path having an output spliced at 45° to an input of a birefringent fiber of a phase modulator, so that light of both channels of said reference path is equally coupled into the slow axis of said phase modulator input birefringent fiber.

29. The birefringent optical fiber reference path as recited in claim 28, wherein the phase modulator comprises a lithium niobate Y-waveguide electro-optic phase modulator.

30. The birefringent optical fiber reference path as recited in claim 28, wherein said phase modulator has two phase modulator arms that are respectively driven with different frequencies to generate frequency multiplexed optical signals, and a detector path associated with the birefringent optical fiber reference path is provided with a digital filter for separating the frequency multiplexed signals.

* * * * *

UNITED STATES PATENT AND TRADEMARK OFFICE
CERTIFICATE OF CORRECTION

| | |
|---|---|
| PATENT NO. | : 6,665,456 B2 |
| APPLICATION NO. | : 10/044421 |
| DATED | : December 16, 2003 |
| INVENTOR(S) | : Digant P. Dave et al. |

It is certified that error appears in the above-identified patent and that said Letters Patent is hereby corrected as shown below:

Column 1, line 12: Insert -- This invention was made with government support under DK059472 awarded by the National Institute of Health. The government has certain rights in the invention. --

Signed and Sealed this

Twenty-first Day of April, 2009

JOHN DOLL
*Acting Director of the United States Patent and Trademark Office*